Figure 1:
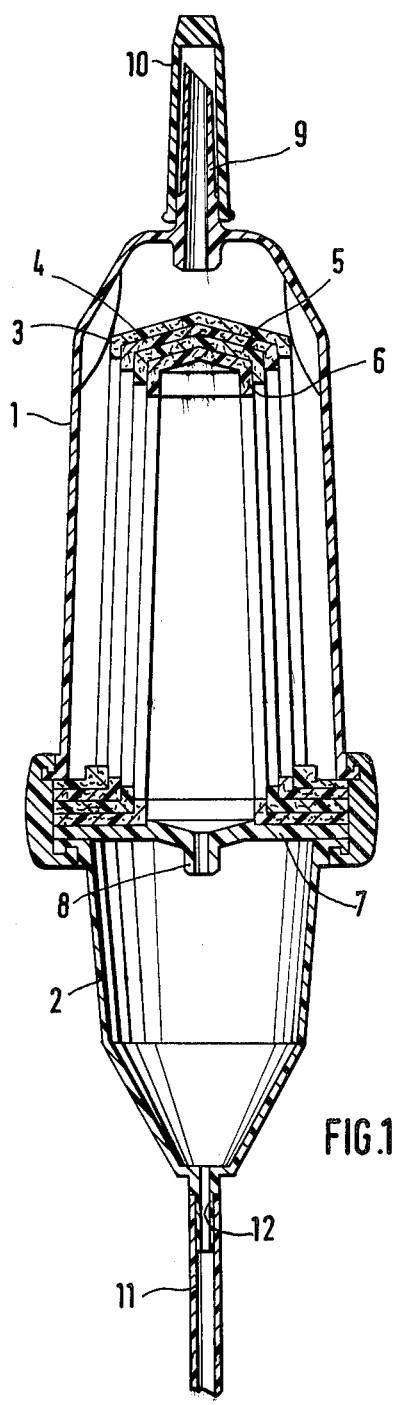

United States Patent [19]

Rosemeyer et al.

[11] 4,087,363
[45] May 2, 1978

[54] FILTER FOR BLOOD

[75] Inventors: Friedrich Rosemeyer, Urberach; Wolfram Hubert Walker, Oberroden; Karl-Heinz Gänshirt, Sprendlingen und; Heinz Wendt, Senden, all of Germany

[73] Assignee: Biotest-Serum-Institut GmbH, Frankfurt, M.-Niederrad, Germany

[21] Appl. No.: 669,052

[22] Filed: Mar. 22, 1976

[30] Foreign Application Priority Data

Mar. 22, 1975 Germany .......................... 7509246[U]
Feb. 26, 1976 Germany ....................... 76057006[U]

[51] Int. Cl.$^2$ ...................... B01D 25/04; B01D 39/16
[52] U.S. Cl. .................................... 210/315; 210/338; 210/342; 210/448; 210/489; 128/DIG. 23; 128/214 C
[58] Field of Search ............ 128/214 R, 214 C, 214.2; 210/314, 337, 338, 342, 446, 448, 489, 490, 315, 316, DIG. 23

[56] References Cited

U.S. PATENT DOCUMENTS

| | | | |
|---|---|---|---|
| 2,186,987 | 1/1940 | Nesset | 128/214 C |
| 2,442,818 | 6/1948 | Lyman | 210/338 X |
| 2,644,586 | 7/1953 | Cutter | 210/314 |
| 2,696,818 | 12/1954 | Van Loghem | 128/214 C |
| 2,879,784 | 3/1959 | Cutter | 128/214 C X |
| 3,003,643 | 10/1961 | Thomas | 210/314 X |
| 3,765,536 | 10/1973 | Rosenberg | 210/446 |
| 3,935,111 | 1/1976 | Bentley | 210/446 |
| 4,035,304 | 7/1977 | Watanabe | 210/DIG. 23 |

Primary Examiner—Charles N. Hart
Assistant Examiner—Robert H. Spitzer
Attorney, Agent, or Firm—Burgess, Dinklage & Sprung

[57] ABSTRACT

A filter for blood comprising a pair of members together forming a housing with an inlet and an outlet, an aperture diaphragm between said members across the interior of said housing and dividing said housing into a filter chamber and a drip chamber respectively communicating with said inlet and outlet, means forming a hermetic and sterile seal between said members, and a plurality of filter elements serially disposed within said housing so that blood being filtered therethrough must pass in sequence through said inlet, through all of said filter elements, through the aperture of said diaphragm and then through said outlet. Preferably at least four woven nylon screens are employed as the filter elements in a nylon housing, the filter elements in the direction of flow successively having screen sizes of about 200 $\mu$, 50 $\mu$, 20 $\mu$ and 10 $\mu$.

3 Claims, 2 Drawing Figures

FILTER FOR BLOOD

The present invention relates to a filter for blood, particularly during transfusions, for removal of microaggregates which form during the stabilization and preservation of blood and liquid blood constituents during storage.

It is known that these microaggregates cannot be removed with customary filters having screen sizes between 170 and 200 $\mu$ because the microaggregates, which consist mostly of thrombocytes, leucocytes, erythrocytes and their fragments, as well as fibrin and denatured proteins, vary in number, size and composition depending on the storage conditions plus a number of other factors. However, these aggregates can lead to lung emboli through clogging of the capillary vessels of the lung.

While there are already fine filters having screen sizes of below 170 $\mu$, these have an unsatisfactory filtering speed.

It is accordingly an object of the invention to provide a blood filter of relatively high capacity and filtering speed suitable for use during transfusion of blood.

These and other objects and advantages are realized in accordance with the present invention pursuant to which there is provided a filter comprising a pair of members together forming a housing with an inlet and an outlet, an aperture diaphragm between said members across the interior of said housing and dividing said housing into a filter chamber and a drip chamber respectively communicating with said inlet and outlet, means forming a hermetic and sterile seal between said members, and a plurality of filter elements serially disposed within said housing so that blood being filtered therethrough must pass in sequence through said inlet, through all of said filter elements, through the aperture of said diaphragm and then through said outlet.

Advantageously at least two filters are provided having different screen sizes, the filter of larger screen size being positioned upstream of the filter of smaller screen size. There may be as many as five or even more filters with flow taking place inwardly or outwardly but first contacting the filter of largest screen size and then the finer filters. The filter housing is sealed hermetically and sterilely, i.e. gas-tight and germ-tight, preferably by injection molding.

The individual filtering stages of the new transfusion filter are separated from each other and sealed in such a manner that the purified filtrate present in each case in the individual cascade can no longer mix with the filtrate of a different filtering stage.

A specific gradation of the fineness of the filters of the individual inserts makes it possible to regulate the loading of the filter inserts in such a manner that all have almost equal loadings.

In a preferred embodiment the first filter has, for instance, a screen size or pore diameter of about 200 $\mu$, the next about 50 $\mu$, the next about 20 $\mu$ and finally about one or two of about 10 $\mu$.

All ordinary filter materials for similar purposes are suitable as filter materials for the cascade or serial filters. Preferably there are employed synthetic filter materials compatible with blood, such as polyamides (nylon), polyolefins, and the like. In a preferred embodiment of the invention, the filter elements and housing are composed of the same synthetic material, especially nylon.

Advantageously, the filter elements are woven screens since they preclude adsorption of the material to be filtered.

Figure 2:
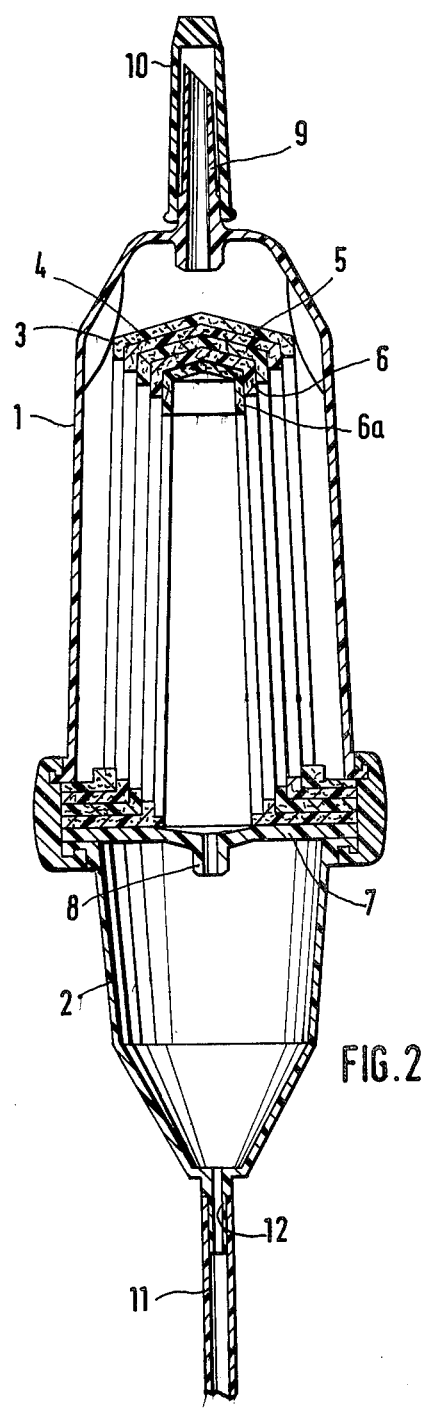

The invention will be further explained with reference to the accompanying drawings, wherein:

FIG. 1 is vertical section through one embodiment of the new transfusion filter, and FIG. 2 is a vertical section through another embodiment.

Referring now more particularly to the drawings, the new device consists of a two-part housing with filter chamber 1 and drip chamber 2 held together by an annular ring. In the filter chamber 1 there are arranged up to five filters with differing surfaces 3, 4, 5, 6 and 6a in the form of a cascade.

A diaphragm 7 is secured in position between the filter and drip chambers 1 and 2, respectively, and it is provided with a drip aperture 8. An injection pin 9 is provided at the blood inlet on the upper housing portion 1 to tap the container for the blood supply. Prior to use a protective cap 10 covers the pin 9.

The portion 2 of the housing serving as drip chamber prevents air from entering the discharge tube 11 and thereby the vein of the receiver with formation of an air embolism. The discharge tube 11 is connected to an outlet 12 on the lower housing part 2. This discharge tube 11 can terminate in known manner in an injection insert which consists, for instance, of latex and makes it possible to inject medicaments into the blood stream.

As noted, in a preferred embodiment filter 3 has a screen size or pore diameter of about 200 $\mu$, filter 4 about 50 $\mu$, filter 5 about 20 $\mu$ and filter 6 about 10 $\mu$. A fifth filter 6a, as shown in FIG. 2, can have, for instance, a pore diameter of about 8 to 10 $\mu$. Additional filter elements have only minimal further effect.

The new filters can be used once for a single container of blood, plasma or serum, or for several containers, but their simplicity and low cost permits their being discarded after a single use rather than going through disassembly, re-sterilization and re-assembly. The large filtering surface permits filtration to proceed at a rate commensurate with that of transfusions so that the filter does not constitute a bottleneck in the transfusion procedure.

It will be appreciated that the instant specification and examples are set forth by way of illustration and not limitation, and that various modifications and changes may be made without departing from the spirit and scope of the present invention.

What we claim is:

1. A filter for blood comprising a pair of members together forming a housing with an inlet and an outlet, an apertured diaphragm between said members across the interior of said housing and dividing said housing into a filter chamber and a drip chamber respectively communicating with said inlet and outlet, means forming a hermetic and sterile seal between said members, and four filter elements each in the form of a woven screen and having respective screen sizes of about 200$\mu$, 50$\mu$, 20$\mu$ and 10$\mu$ with the openings in each screen being uniform in size, the screens being serially disposed within said housing in order of descending screen size in the downstream so that blood being filtered therethrough must pass in sequence through said inlet, through all of said filter elements of progressively smaller screen size, through the aperture of said diaphragm and then through said outlet whereby said filter is capable of passage of blood therethrough at a high filtration rate.

2. A filter according to claim 1, wherein the members and filters are formed of the same polymeric material.

3. A filter according to claim 2, wherein said polymeric material is nylon.

* * * * *

UNITED STATES PATENT AND TRADEMARK OFFICE
CERTIFICATE OF CORRECTION

PATENT NO. : 4,087,363
DATED : May 2, 1978
INVENTOR(S) : Friedrich Rosemeyer et al It is certified that error appears in the above-identified patent and that said Letters Patent are hereby corrected as shown below:

Col. 2, line 57    After "downstream" insert --direction--.

Signed and Sealed this

Twenty-first Day of November 1978

[SEAL]

Attest:

RUTH C. MASON
*Attesting Officer*

DONALD W. BANNER
*Commissioner of Patents and Trademarks*